United States Patent [19]
Massoud et al.

[11] Patent Number: 5,313,044
[45] Date of Patent: May 17, 1994

[54] METHOD AND APPARATUS FOR REAL-TIME WAFER TEMPERATURE AND THIN FILM GROWTH MEASUREMENT AND CONTROL IN A LAMP-HEATED RAPID THERMAL PROCESSOR

[75] Inventors: Hisham Z. Massoud; Ronald K. Sampson, both of Durham, N.C.

[73] Assignee: Duke University, Durham, N.C.

[21] Appl. No.: 874,812

[22] Filed: Apr. 28, 1992

[51] Int. Cl.$^5$ .............................................. B23K 26/00
[52] U.S. Cl. ........................... 219/121.85; 219/121.83
[58] Field of Search ........... 219/121.6, 121.83, 121.85; 437/7, 8

[56] References Cited

U.S. PATENT DOCUMENTS

| | | | |
|---|---|---|---|
| 4,649,261 | 3/1987 | Sheets | 219/390 |
| 4,680,451 | 7/1987 | Gat et al. | 219/411 |
| 4,698,486 | 10/1987 | Sheets | 250/492.2 |
| 4,778,270 | 10/1988 | Kinney et al. | 356/43 |
| 4,857,689 | 8/1989 | Lee | 219/10.71 |
| 4,890,933 | 1/1990 | Amith et al. | 374/121 |
| 4,891,499 | 1/1990 | Moslehi | 219/502 |
| 4,919,542 | 4/1990 | Nulman et al. | 374/9 |
| 4,924,073 | 5/1990 | Chiba | 219/413 |
| 4,956,538 | 9/1990 | Moslehi | 219/121.6 |
| 4,975,561 | 12/1990 | Robinson et al. | 219/390 |
| 4,984,902 | 1/1991 | Crowley et al. | 219/121.6 |

OTHER PUBLICATIONS

Massour et al.; Principles of Wafer Temperature Measurment Using in situ Ellipsometry, Electrochemical Society Conference, Spring 1991.
Sampson et al.: Simulatneous Measurement of Wafer Temperature and Native Oxide Thickness Using In Situ Ellipsometry, Electrochemical Society Conference, Spring, 1991.
Hauge et al., Design and Operation of Eta, An Automated Ellipsometry; IBM Journal of Research and Development, pp. 472-489 (1973).
van der Muelen et al.; Design and Operation of an Automated High Temperature Ellipsometer; Journal of the Optical Society of America, vol. 64, No. 6, pp. 804-811 (1984).
Kroesen et al.; Nonintrusive Wafer Temperature Measurement Using In Situ Ellipsometry, Journal of Applied Physics, pp. 3390-3392 (1991).
Tomita et al., A New Non-Contact Method to Measure Temperature of the Surface of Semiconductor Wafers, Japanese Journal of Applied Physics, vol. 25, No. 11, pp. L925-L927 (1986).
Yu et al. Using in situ Ellipsometry for Film Thickness Endpoint Control, Semiconductor International, pp. 166-169, (May 1991).
Laura Peters, Why You Need Rip, Semiconductor International, pp. 72-74 (1991).
John et al., In Situ Spectroscopic Ellipsometry for Real Time Semiconductor Growth Monitor Material Research Society Symposium, vol. 216 (1991).
Aspnes et al., Real-Time Optical Diagnostics for Measuring and Controlling Epitaxial Growth: Material Research Society Symposium, vol. 222 (1991).
Johs et al., Real-Time Analysis of In-Situ Spectroscopie Ellipsometric Data During MBE Growth of III-V Semiconductors, Material Research Society Symposium, vol. 222 (1992).
Yao et al.; In-Situ Measurement of GaAs Optical Constants and Surface Quality, as Functions of Temperature, Material Research Society Symposium, vol. 222, (1991).

*Primary Examiner*—C. L. Albritton
*Attorney, Agent, or Firm*—Richard E. Jenkins

[57] ABSTRACT

An ellipsometer measures/monitors the change in polarization of light upon reflection from a wafer sample. The temperature of the wafer substrate surface and the film thickness are then simultaneously determined in situ using ellipsometry where the true wafer temperature is determined in real-time by the computer from a calculation based on the known temperature dependence of the refractive index of the wafer. The power output to the lamps is then adjusted accordingly to raise or lower the wafer temperature within the apparatus. This process continues automatically to maintain the desired temperature and film growth rate until the desired film thickness is achieved.

9 Claims, 5 Drawing Sheets

METHOD AND APPARATUS FOR REAL-TIME WAFER TEMPERATURE AND THIN FILM GROWTH MEASUREMENT AND CONTROL IN A LAMP-HEATED RAPID THERMAL PROCESSOR

TECHNICAL FIELD

This invention relates to semiconductor processing in general, and in particular to a method and apparatus for precise real-time wafer temperature and thin film growth measurement and control using in situ ellipsometry in a single-wafer lamp-heated rapid thermal processor (RTP).

RELATED ART

In a single wafer rapid thermal processing (RTP) system, the most critical process variables are the wafer temperature and the thickness of any film or films present, growing or being deposited or etched on the wafer. As a result there has been a long felt need for an apparatus and method to simultaneously measure the wafer temperature and film thickness in real time in a non-invasive, fast, and reliable manner. In addition, the apparatus and method must also provide reproducible and process independent measurements.

Typically, optical pyrometry has been used as a non-contact technique for measuring the wafer temperature by first measuring the amount of infrared radiation emitted by the wafer and then converting it to a temperature. However, the accuracy and reproducibility of optical pyrometers are very sensitive to the optical properties of the surface (i.e., the emissivity of the surface), interference from the lamps, the process environment, and the type of process occurring in the system. Although several emissivity compensation schemes have been developed to try and account for these variations, the temperature control needed to control and repeat the processes required in the fabrication of integrated circuits has not been achieved.

In addition to the need for accurate temperature measurement and control, it is also necessary to accurately determine the thickness of a film being deposited, grown or etched at a particular temperature. Ellipsometry is a technique that has been widely applied to the study of surface films and has been used to characterize the optical constants of the surfaces of a variety of materials. However, it has not previously been applied to simultaneous temperature and film growth measurement and control. This is due in part to the fact that it has not been previously known to be possible to separate the effects of heating from the effects of film growth/deposition in the measured optical constants using this technique.

SUMMARY OF THE INVENTION

The present invention described herein comprises a method and apparatus for simultaneous, precise real-time wafer temperature and thin film growth measurement and control in a rapid thermal processing system, which substantially eliminates or reduces the problems associated with conventional temperature sensing methods and film thickness process control. The present invention allows the monitoring and adjustment of the temperature of a wafer and the monitoring of film thickness and growth rates, if applicable, in an RTP system in situ on a real-time basis with a high degree of accuracy and repeatability.

It is a technical advantage of the present invention that the temperature and surface film thickness of a wafer may be accurately and precisely measured simultaneously on a real-time basis throughout the operating temperature range of a RTP system (i.e., 0°–1100° C.).

It is a further technical advantage that this technique is independent of the emissivity of the wafer which can vary significantly and unpredictably within a typical rapid thermal process.

It is a further technical advantage that the wafer temperature may be adjusted if necessary on a real-time basis.

It is still a further technical advantage that the film thickness and growth can be simultaneously monitored and the growth rate adjusted if necessary along with the temperature on a real-time basis.

BRIEF DESCRIPTION OF THE DRAWINGS

For a more complete understanding of the nature and objects of the present invention, reference is now made to the following detailed description, taken in conjunction with the accompanying drawings, in which.

DETAILED DESCRIPTION OF THE INVENTION

Figure 1:
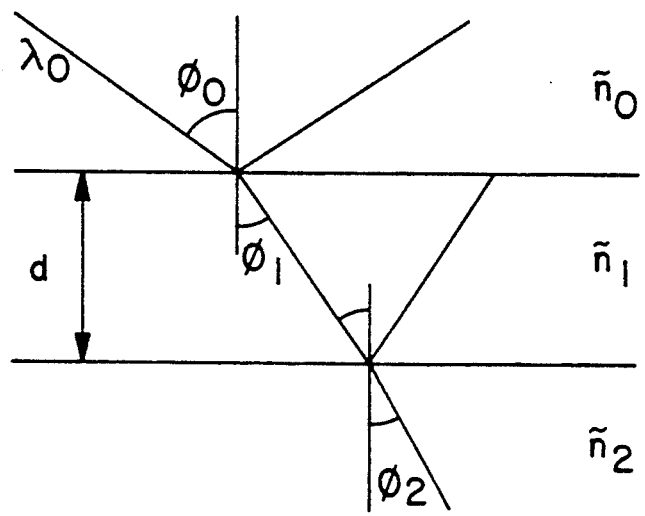
FIG. 1 is a drawing showing the reflection and refraction of light at a planar thin film on a substrate.

As a general background explanation of the relationship between the optical constants of a material and $\psi$ and $\Delta$ as measured by an ellipsometer, it should be appreciated that the optical constants such as the refractive indices and thicknesses of surface films can be related to the measured change in polarization of light as it is reflected from the material surface. When linearly polarized light undergoes reflection from a material such as a semiconductor wafer, both the magnitude and phase of this polarization changes such that the reflected light is, in general, elliptically polarized.

This change in polarization is directly related to the optical constants of the material surface, such as the complex refractive index of the material substrate, the refractive index and thickness of any films present, and the refractive index of the medium. In addition, this change in polarization is dependent upon the wavelength and angle of incidence of the polarized light. These absolute changes in the amplitude and phase, described in terms of the Fresnel coefficients for parallel and normal components of the light upon reflection, can be obtained from the overall reflection and transmission coefficients for the material.

For the case of a material with a single film of index $n_1$ on a substrate with a refractive index $n_2$ immersed in a medium with an index $n_0$ such as air or a vacuum as illustrated in FIG. A, the overall reflection $\rho$ and transmission $\tau$ coefficients are given by $$\rho(v) = \frac{r_{01(v)} + r_{12(v)}e^{-2i\delta}}{1 + r_{01(v)}r_{12(v)}e^{-2i\delta}} \quad (1)$$

and $$\tau(v) = \frac{t_{01(v)}t_{12(v)}e^{-i\delta}}{1 + r_{01(v)}r_{12(v)}e^{-2i\delta}}, \quad (2)$$

where $r_{ij}$ and $t_{ij}$ are the reflection coefficients between media i and j for parallel (v=p) and normal (v=s) components of the incident light and are given by $$r_{ij(p)} = \frac{\bar{n}_i \cos\phi_j - \bar{n}_j \cos\phi_i}{\bar{n}_i \cos\phi_j + \bar{n}_j \cos\phi_i} \quad (3a)$$

$$t_{ij(p)} = \frac{2\bar{n}_i \cos\phi_i}{\bar{n}_i \cos\phi_j + \bar{n}_j \cos\phi_i} \quad (3b)$$

$$r_{ij(s)} = \frac{\bar{n}_i \cos\phi_i - \bar{n}_j \cos\phi_j}{\bar{n}_i \cos\phi_i + \bar{n}_j \cos\phi_{ij}} \quad (4a)$$

and $$t_{ij(s)} = \frac{2\bar{n}_i \cos\phi_i}{\bar{n}_i \cos\phi_j + \bar{n}_j \cos\phi_j} \quad (4b)$$

where $\theta_i$ and $\theta_j$ are the angles as illustrated in FIG. 1, and the change in phase $\delta$ of the beam traversing the film is given by $$\delta = \frac{2\pi d}{\lambda}(n_1^2 - \sin^2\phi_0)^{\frac{1}{2}}, \quad (5)$$

where d is the film thickness, $\lambda$ is the wavelength of light, $n_1$ is the index of the film, and $\theta_0$ is the angle of incidence.

The relationship between the overall reflection coefficients and the measured ellipsometric parameters $\psi$ and $\Delta$ is then given by the fundamental equation of ellipsometry $$e^{i\Delta}\tan\psi = \frac{\rho(p)}{\rho(s)}, \quad (6)$$

where $\psi$ and $\Delta$ are the measured ellipsometric parameters corresponding to the change in magnitude and phase, respectively, of the light upon reflection. Since the behavior of the parallel and normal components of the light upon reflection is a function of the optical constants of the material, the optical constants can be determined from the experimentally determined ellipsometer parameters $\psi$ and $\Delta$. The solution to these relationships is in general transcendental, such that a numerical or graphical technique is then applied to obtain the optical constants (i.e. the refractive index of the substrate) of the material at a particular wavelength and angle of incidence.

Figure 2:
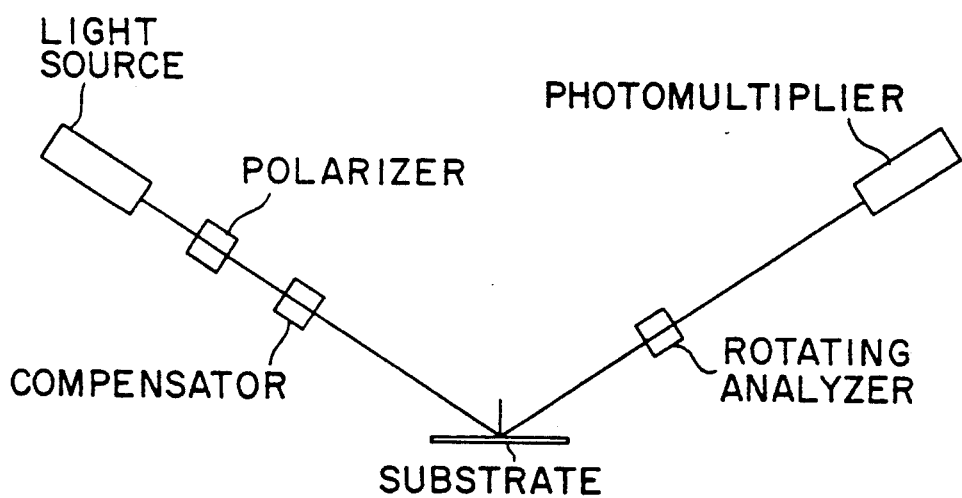
FIG. 2 is a drawing showing a schematic of a typical rotating analyzer ellipsometer (RAE).

Experimental determination of the ellipsometric parameters $\Psi$ and $\Delta$ can be summarized by the following sequence of steps, assuming a rotating analyzer ellipsometer (RAE) as illustrated in FIG. 2 is used, which is common for automatic ellipsometric measurements.

However, it should be noted that many types of ellipsometers can be used for measuring $\psi$ and $\Delta$.

First the light emitted from the light source such as a laser is linearly polarized at a known angle to the plane of incidence by the polarizing prism. The parallel and normal components of the linearly polarized light are then shifted 90° with respect to each other by a compensator in order to increase sensitivity of the ellipsometer to the optical constants of substrates that have thin (i.e. <500Å) surface films. Again, it should be noted that a compensator is not essential for the determination of $\psi$ and $\Delta$. The linearly polarized, phase-shifted light is then reflected off the sample which has the effect of changing the polarization such that in general, the light becomes elliptically polarized. The reflected light is then analyzed by the rotating analyzing prism rotating an angle $\theta$ in a time t, that converts the reflected polarized light into light intensity vs. analyzing angle $\theta$. This light intensity vs. $\theta$ is then converted to a current varying sinusoidally with time, where the time t is directly proportional to the analyzing angle $\theta$. This current signal can then be amplified and converted to a voltage signal, where it can then be sampled and converted to a digital signal for manipulation within a computer. Once sampled data corresponding to a complete revolution of the analyzer is stored in the computer, a fast Fourier transform (FFT) can be performed to obtain the second order coefficients of the sine and cosine Fourier expansion terms of the form $$I(\theta) = I_0[1 + a_2\cos(2\theta) + b_2\sin(2\theta)]. \quad (7)$$

where $I_0$ is the average intensity, and $a_2$ and $b_2$ are the second order coefficients. Calculation of the ellipsometric parameters $\psi$ and $\Delta$ is then given by $$\psi = \frac{1}{2}\cos^{-1}(-a_2) \quad (8)$$

and $$\Delta = \cos^{-1}\left(\frac{b_2}{\sqrt{1 - a_2^2}}\right). \quad (9)$$

Alternatively, $a_2$ and $b_2$ can be used to calculate the overall reflection coefficients $$\frac{\rho(p)}{\rho(s)}$$

and $\psi$ and $\Delta$ calculated from $$\frac{\rho(p)}{\rho(s)}$$

according to Eq. 6 above. Once $\psi$ and $\Delta$ have been measured, Eq. 6 can be solved to obtain the desired optical constants of the sample.

Applicants have described hereinabove how an ellipsometer measures $\psi$ and $\Delta$ and the relationship between the optical constants of the material being evaluated and the measured parameters $\psi$ and $\Delta$. Applicants will describe hereinafter their discovery of the relationship between $\psi$ and $\Delta$ and the material substrate temperature and the thickness of a surface film. When the temperature of a substrate such as a silicon wafer is raised (e.g., by lamp heating), the refractive index changes to reflect the increase in thermal energy of the substrate. In addition to this dependence on temperature, the refractive index is also dependent upon the composition of the substrate, the wavelength $\lambda$ of light, and the angle that the light impinges the substrate surface (i.e. the angle of incidence, $\theta_0$). However, for a material of known composition, a particular wavelength and angle of incidence, such as is obtained when using a laser light source mounted in a fixed position with respect to the substrate surface of known composition, the refractive index becomes only a function of temperature.

Figure 3:
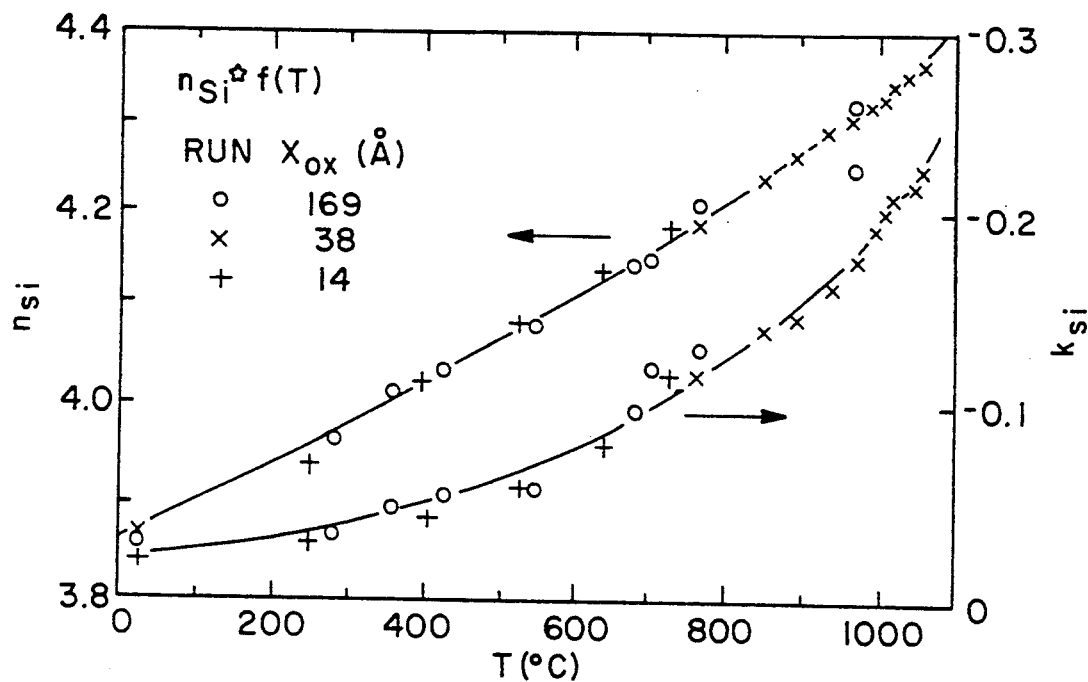
FIG. 3 is a drawing showing temperature dependence of the real $n_{Si}$ and imaginary $k_{Si}$ components of the refractive index of silicon for $\lambda = 6328$ Å and $\phi = 70°$.

More specifically, for the case of a silicon wafer and an ellipsometer using a helium-neon gas laser operating at a wavelength of 6328Å and fixed at an angle of incidence of 70°, the temperature dependence of the refractive index is strong and well known. FIG. 3 is a plot of the real ($n_{Si}$) and imaginary ($K_{Si}$) components of the complex refractive index of silicon ($n_{Si}=n_{Si}-iK_{Si}$) as functions of temperature for this particular set of parameters as measured by Y. J. van der Muelen and N. C. Hien and published in the *Journal of the Optical Society of America* in Volume 64 on page 810 in June of 1974. As is illustrated, both the real and imaginary components increase monotonically with increasing temperature.

Given the relationships illustrated in FIG. 3, it is then possible to fit both components of the refractive index to obtain functions dependent upon temperature by using a standard least squares fitting approach to obtain two polynomials of the form $$n_{Si}=n(T), \quad (10)$$

and $$\kappa_{Si}=\kappa(T). \quad (11)$$

Figure 4:
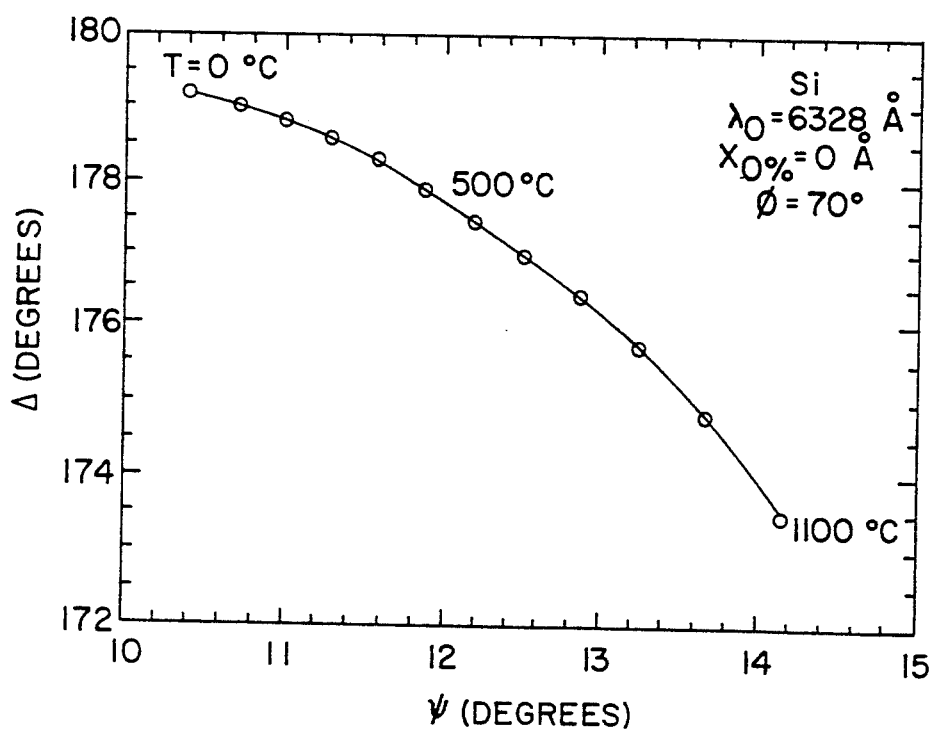
FIG. 4 is a drawing showing behavior of $\psi$ and $\Delta$ for varying temperature for a bare silicon wafer.

The ellipsometric parameters $\psi$ and $\Delta$ can also be determined as functions of temperature by applying the polynomials of Eqs. 10 and 11 to Eq. 6 and solving for $\psi$ and $\Delta$, where for the case of a silicon wafer which does not have a film on its surface (i.e. $d=0$ in Eq. 3), the result is illustrated in FIG. 4.

The behavior of $\psi$ and $\Delta$ can now be generalized to include the effects of surface films (i.e. $d\neq 0$ in Eq. 5). The result for the case where the surface film refractive index is $n_{ox}=1.46$, which is between typical values of 1.0 to 4.0 and corresponds to silicon dioxide is plotted in FIG. 5. As can be seen, both the temperature and film thickness are uniquely determined by a single measured set of $\psi$ and $\Delta$.

Figure 5:
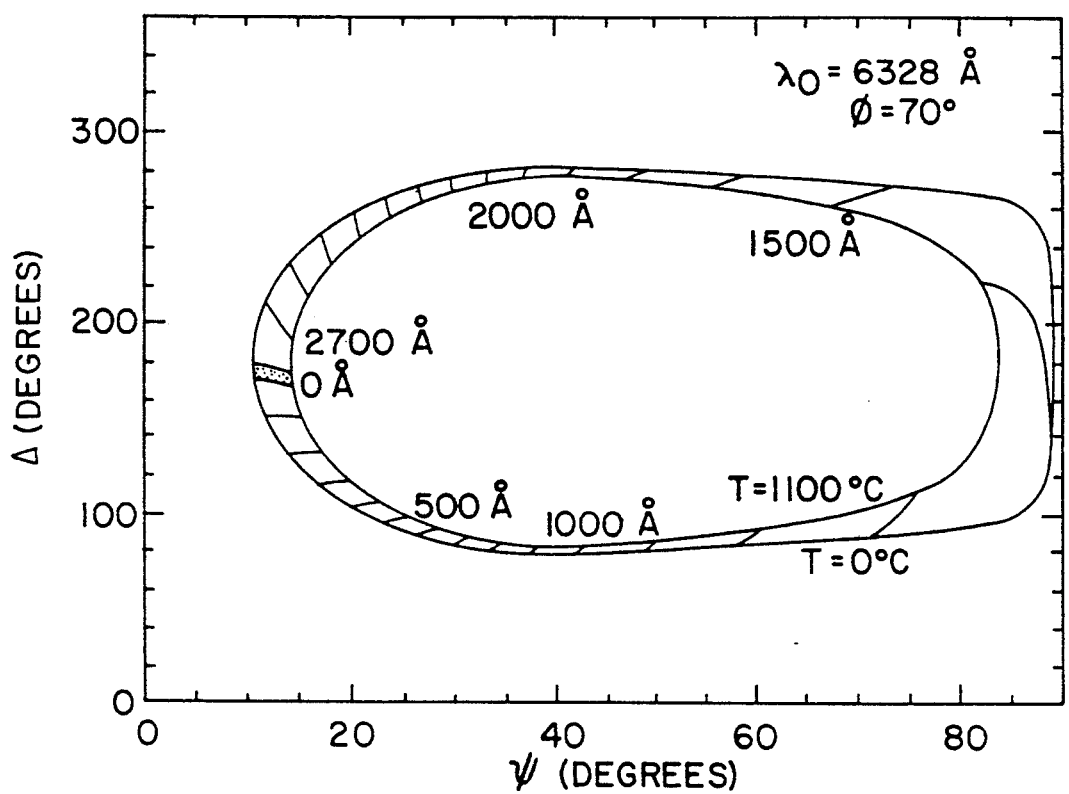
FIG. 5 is a drawing showing behavior of $\psi$ and $\Delta$ for varying temperatures and oxide thicknesses for $n_{ox} = 1.46$.

Therefore as illustrated in FIG. 5, the temperature and film thickness can be calculated directly from the measured parameters $\psi$ and $\Delta$ by using a similar least squares algorithm to obtain polynomials of the form $$T=T(\psi,\Delta) \quad (12)$$

and $$X_f=X_f(\psi,\Delta), \quad (13)$$

where these polynomials have been generated for a particular wavelength, angle of incidence, substrate composition, and film refractive index. Thus, this technique depends on the above-described parameters only, which unlike the wafer emissivity, are usually process independent. In addition, these polynomials are readily incorporated into a computer for fast calculation of the temperature and film thickness given $\psi$ and $\Delta$.

In the event that the refractive index of the film is unknown, or several films of arbitrary thicknesses are present on the surface of the substrate, multiple wavelength or spectroscopic ellipsometry can be applied and measurements at different wavelengths taken, such that the unknown optical constants or composition of the unknown films of interest are uniquely determined. Or alternatively, a measurement at a single wavelength can be made at a known temperature, such as at room temperature, to obtain the unknown refractive index and/or composition of the film. Then the polynomials corresponding to the measured refractive index/composition can be used to control temperature and film growth in subsequent process steps.

Assuming a single wavelength measurement of a substrate with at most one surface film of known refractive index, the temperature and film thickness can be determined by first measuring the ellipsometric parameters $\psi$ and $\Delta$, and then applying the polynomials in Eqs. 12 and 13. The alternative approach, although not as fast but more general, is to first measure $\psi$ and $\Delta$ and then solve for the temperature and film thickness by solving Eq. 6 and including all the necessary optical constants of any films present before the thermal process begins. Thus, the temperature and the film thickness can be determined from the polynomials described above or by solving Eq. 6 for any arbitrary temperature encountered in a rapid thermal processor (i.e. $0 \leq T \leq 1100°$ C.).

Therefore, the present invention utilizes an ellipsometer to determine the ellipsometric parameters $\psi$ and $\Delta$ in real-time by measuring the change in polarization of light as it is reflected from the surface of the wafer. Once $\psi$ and $\Delta$ have been determined, the temperature and film thickness can be accurately calculated. Having an accurate and real-time measurement of the temperature of the wafer allows an appropriate adjustment of the heating lamps to provide the desired wafer temperature or thermal cycle. Additionally, having an accurate and real-time measurement of the thickness of a film on the surface of the wafer allows appropriate adjustment of the heating lamps to provide the desired film growth rate and final film thickness.

In accordance with one aspect of the invention, an apparatus determines the amount of any background radiation present within the system that may reduce the signal to noise ratio of the measurement and subtracts it accordingly. A shutter is properly positioned after the polarizing prism that blocks the polarized light source, thus enabling measurement of the intensity of the background radiation. Therefore, the wafer temperature can be determined with significantly reduced interference from any direct or indirect radiation present within the system.

In another aspect of the present invention the transparent optical ports that are used to pass light into the process chamber to probe the sample are attached to the process chamber such that the light emitted from the light source is incident normally to the optical ports, while maintaining a fixed angle of incidence $\phi_o$ with the wafer. These optical ports also serve to isolate the ellipsometer from the process ambient.

Figure 6:
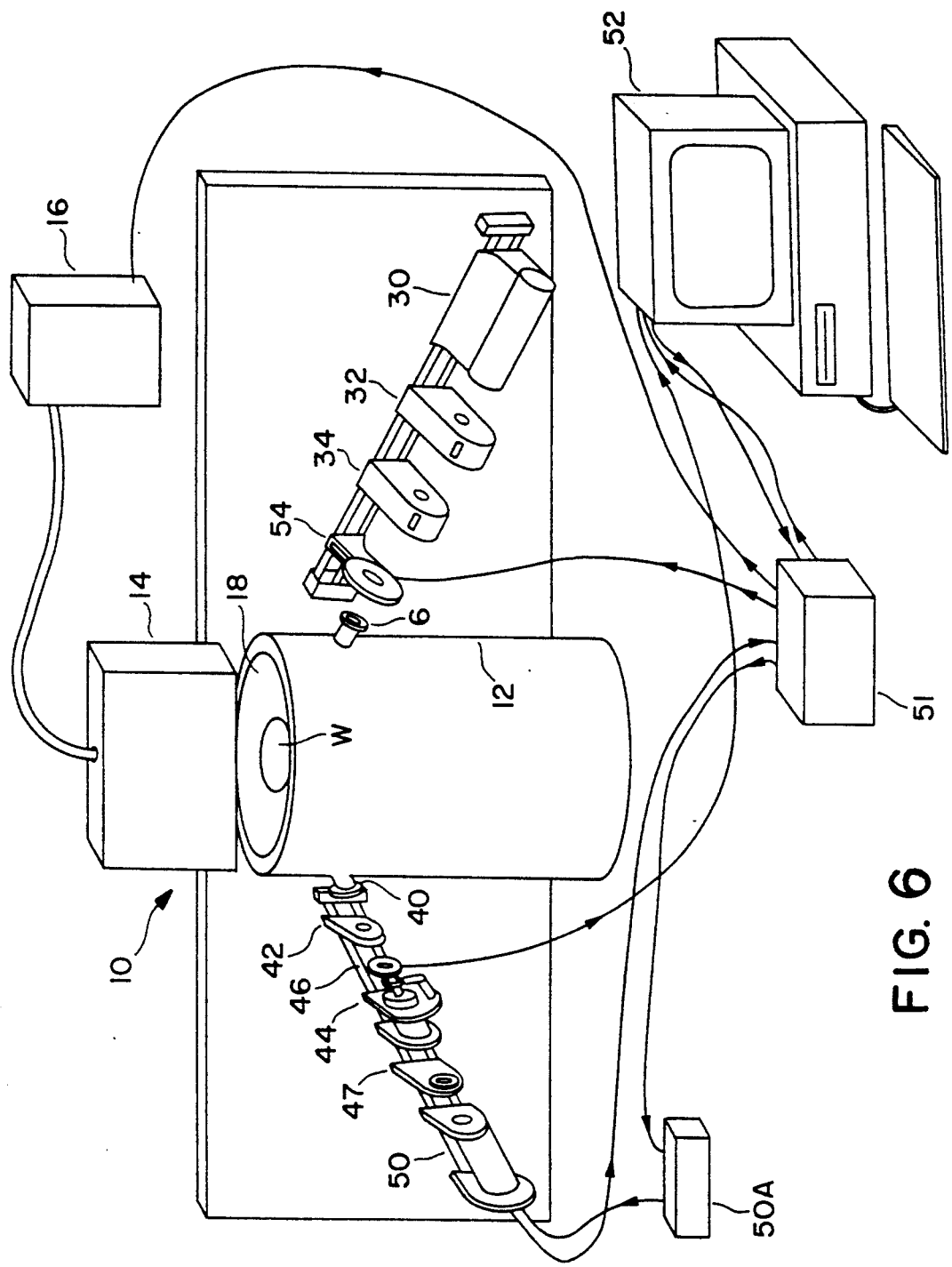
FIG. 6 is a perspective view of an apparatus constructed in accordance with the present invention.
Figure 7:
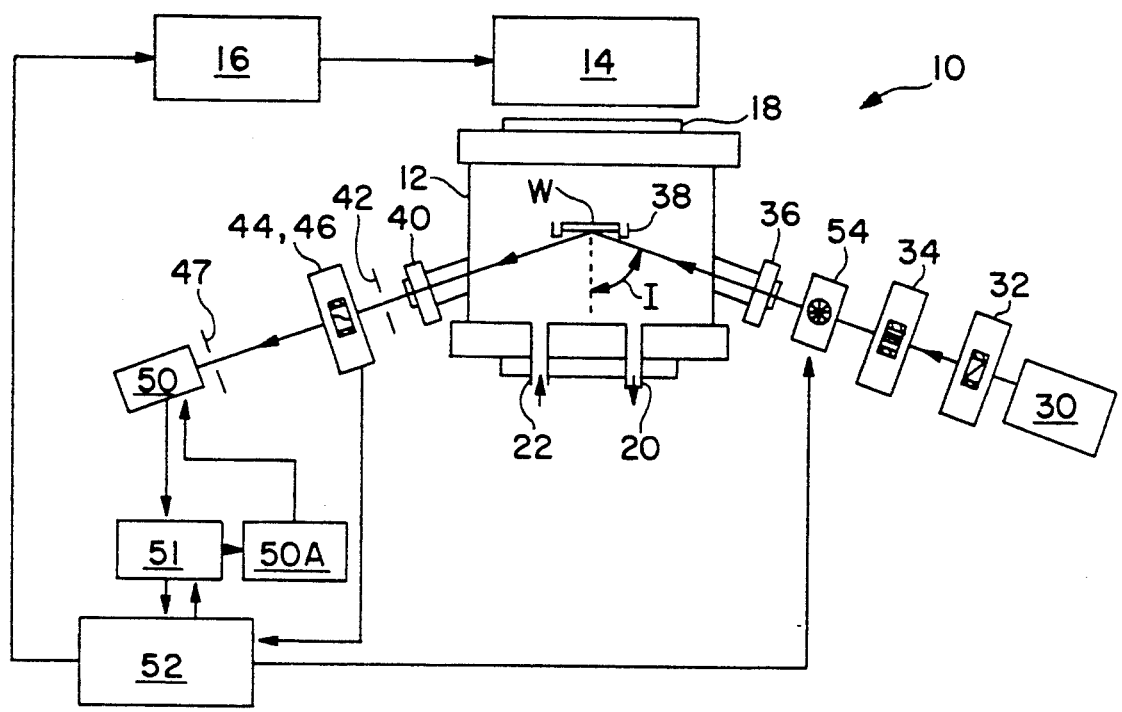
FIG. 7 is a schematic diagram of an apparatus constructed in accordance with the present invention.

Referring now to FIGS. 6 and 7, an apparatus constructed in accordance with the present invention is generally designated by the reference numeral 10. The apparatus 10, a single wafer rapid thermal processing system, comprises a single wafer rapid thermal processing (RTP) chamber 12 having a one-sided heating lamp module 14 (such as a bank of tungsten-halogen heating elements) controlled by the lamp power controller 16. The apparatus 10 is used for semiconductor wafer processing such as for rapid thermal annealing, rapid thermal oxidation, and chemical vapor deposition processes.

As fabrication processes within RTP chamber 12 are dependent upon temperature, and the wafer heating required for the processing is provided by lamp module 14 and lamp power controller 16, which are readily available from commercial sources. Lamp module 14 typically comprises an air and water cooled metallic shroud and reflector having both water and air inlet and outlet pipes (not shown) for coolant circulation. The shroud serves to cool lamp module 14 and provides an optical reflector (not shown) on its bottom surface for a bank of lamps such as tungsten-halogen lamps (not shown). The wafer is therefore heated by radiation emitted from the lamps that passes through a quartz window 18. The wafer may be heated in a vacuum provided by a vacuum system 20 or in any desired ambient gas 22 as conceptually illustrated in FIG. 7.

The preferred embodiment of the invention employs an ellipsometer operating at a single wavelength between 0.01 um and 10 um, and a fixed angle of incidence I between 10° and 85°. A specific wavelength of 6328Å is preferred because the optical constants for almost all materials that are used in a RTP system are well-known at this wavelength. Similarly, a specific angle of incidence I of 70° is preferred in order to obtain optimum sensitivity to temperature and film thickness for silicon wafers since silicon wafers are by far the most commonly used in the fabrication of electronic devices. A key feature of the present invention is the application of ellipsometry for simultaneous determination of both the temperature of the wafer and the thickness of any surface film in the RTP system in order to meet the measurement and the process control requirements.

Light is emitted from the ellipsometer light source 30 and linearly polarized by a polarizing prism 32 (such as a Glan-Thomson polarizing prism, which is readily available from a number of commercial sources). For the case in which the ellipsometer light source 30 emits primarily monochromatic light, the preferred embodiment includes the use of a compensator 34 attached after the polarizing prism that serves to shift one component of light 90° in phase with respect to its normal counterpart. The light then passes through a transparent optical port 36 (made of a material such as quartz) at normal incidence with a minimum amount of attenuation and change in polarization. Inside the RTP chamber 23, a wafer W rests on an adjustable holder 38 with its polished side facing downward and oriented such that the light passing through the optical port 36 is incident on the polished side at the preferred angle of incidence. The linearly polarized incident light beam undergoes reflection and is passed out of the RTP chamber 12 through another optical port 40 made of the same material as optical port 36 and oriented such that the reflected light passes through the transparent optical port at normal incidence with a minimum amount of attenuation and change in polarization.

The reflected light then passes through an alignment iris 42 and through the rotating analyzing prism 44 (similar in composition as the polarizing prism) with an attached encoder 46 that provides digital pulses indicating the precise value of the analyzer angle $\theta$ as it rotates in real time. The speed rotation of rotating analyzer prism 44 is set to between 1 Hz and 50 kHz in order to maximize the data acquisition rate and the signal to noise ratio. In the preferred embodiment of this invention, the rotation rate is set to approximately 5 Hz. The analyzed light then passes through another iris and at least one diffuser 47 into a monochromator 48 which is needed only if light source 30 is polychromatic. The light which is monochromatic, diffuse and has an intensity that varies as a function of $\theta$ then enters a suitable detector 50 (such as a photomultiplier tube) where the light intensity is converted into a corresponding output current signal. Detector 50 is powered by power supply 50A.

The output current signal of detector 50 is amplified, filtered and then sampled by an analog to digital and digital to analog converter (A/D) 51 which is also readily available from commercial sources. The digital output signal of A/D converter 51 is fed into computer 52, such as an IBM AT personal computer. Once the set of the digital output signals represents at least one revolution of the rotating analyzer prism with reference to the signal from the encoder, a fast Fourier transform is performed to obtain the second order coefficients of the sine and cosine series. From these coefficients, $\psi$ and $\Delta$ are then calculated using software routines commercially available from a variety of sources. The computer then determines the temperature and film thickness from polynomials obtained as functions of $\psi$ and $\Delta$ by fitting data of $\psi$ and $\Delta$ determined for a particular wafer composition such as silicon, a particular film refractive index such as $n_{ox}=1.46$ for silicon dioxide, a wavelength of light such as $\lambda=6328Å$, and an angle of incidence such as $\phi_0=70°$. The computer then adjusts the power output of the lamp power supply to raise or lower the temperature of semiconductor wafer W by interpreting the measured data according to the desired set values for the wafer temperature and surface film thickness, such as a predetermined set of temperature and film thickness vs. time tables. This adjustment is accomplished by sending a digital lamp signal from computer 52 to analog to digital and digital to analog converter 51 for conversion to an analog signal which is then sent to lamp power controller 16 to cause the lamp power controller to provide more or less power to lamp module 14.

In order to minimize the effects of background radiation, a shutter 54 is controlled by computer 52 such that the light source can be effectively switched off in order to enable a measurement of the background radiation. This measurement, if deemed necessary such as in the measurement of rapid wafer temperature variations, can be used in conjunction with the normal mode of operation to provide an enhanced signal to noise ratio by subtracting the background radiation value from subsequent measurements.

It will be understood that various details of the invention may be changed without departing from the scope of the invention, Furthermore, the foregoing description is for the purpose of illustration only, and not for the purpose of limitation—the invention being defined by the claims.

What is claimed is:

1. A method for determining and adjusting temperature of a semiconductor wafer in a rapid thermal processing system comprising the steps of:
   (a) determining the ellipsometric parameters $\psi$ and $\Delta$ in real-time with an ellipsometer;
   (b) calculating the temperature and film thickness from said ellipsometric parameters of $\psi$ and $\Delta$ of a semiconductor wafer positioned in a thermal processing chamber;

(c) comparing said measured temperature and film thickness to predetermined temperature and film thickness vs. time data; and (d) adjusting the amount of heat provided to said semiconductor wafer by a lamp module in response to said steps (a)-(c).

2. A method according to claim 1 wherein the step of determining the said ellipsometric parameters $\psi$ and $\Delta$ includes the steps of sampling the output signal from an ellipsometer light detector with reference to the signal from a rotating analyzing prism and attached encoder.

3. A method according to claim 1 wherein the step of calculating the temperature and film thickness of the semiconductor wafer from the ellipsometric parameters $\psi$ and $\Delta$ includes the steps of calculating the temperature of said semiconductor wafer by a polynomial previously fitted to the variation of the ellipsometric parameters $\psi$ and $\Delta$ for the wavelength of light emitted from an ellipsometer light source, for the angle of incidence of the light emitted from the light source that impinges on said semiconductor wafer, and for the refractive index of the said film thickness.

4. A method according to claim 1 wherein the step of calculating the temperature and film thickness of said semiconductor wafer from the ellipsometric parameters $\psi$ and $\Delta$ includes the steps of calculating the film thickness of a surface film on said semiconductor wafer by a polynomial previously fitted to the variation of the ellipsometric parameters $\psi$ and $\Delta$ for the wavelength of light emitted from an ellipsometer light source, for the angle of incidence of the light emitted from the light source that impinges on said semiconductor wafer, and for the refractive index of the film thickness.

5. A method according to claim 1 wherein the step of determining the temperature and film thickness of the semiconductor wafer from the ellipsometric parameters $\psi$ and $\Delta$ includes the steps of calculating the complex refractive index of the semiconductor wafer substrate and the film thickness by solving the fundamental equation of ellipsometry for the wavelength of light emitted from the light source of a rotating analyzer ellipsometer, for the angle of incidence of the light emitted from the light source that impinges on said semiconductor wafer, and for the refractive index of the film thickness, wherein the temperature of said semiconductor wafer is determined from a polynomial fitted to the variation of the said complex refractive index of said semiconductor wafer substrate with temperature.

6. A method according to claim 3 or 4 wherein said semiconductor wafer consists essentially of silicon.

7. A method according to claim 3, 4 or 5 comprising utilizing a helium-neon light source and a rotating analyzer ellipsometer operating at a fixed wavelength of 6328Å.

8. A method according to claims 3 or 4 comprising utilizing a fixed angle of incidence of 70°.

9. A method according to claims 3 or 4 utilizing a film refractive index of between 1.0 and 4.0 corresponding to silicon dioxide for a wavelength of light emitted from the light source of 6328Å.

* * * * *